United States Patent [19]

Sleteinger et al.

[11] Patent Number: 4,582,915
[45] Date of Patent: Apr. 15, 1986

[54] PROCESS FOR C-METHYLATION OF 2-METHYLBUTYRATES

[75] Inventors: Meyer Sleteinger, North Plainfield; Thomas R. Verhoeven, Cranford; Ralph P. Volante, East Windsor, all of N.J.

[73] Assignee: Merck & Co., Inc., Rahway, N.J.

[21] Appl. No.: 737,362

[22] Filed: May 23, 1985

Related U.S. Application Data

[63] Continuation of Ser. No. 540,954, Oct. 11, 1983, abandoned.

[51] Int. Cl.$^4$ .............................................. C07D 309/10
[52] U.S. Cl. ...................................... 549/292; 560/256
[58] Field of Search ........................ 549/292; 560/256

[56] References Cited

U.S. PATENT DOCUMENTS

| | | | |
|---|---|---|---|
| 3,983,140 | 9/1976 | Endo et al. | 549/292 |
| 4,231,938 | 11/1980 | Monaghan et al. | 549/292 |
| 4,351,844 | 9/1982 | Patchett et al. | 549/292 |
| 4,490,546 | 12/1984 | Kuo | 549/292 |

FOREIGN PATENT DOCUMENTS 149247 9/1982 Japan .
885044 12/1961 United Kingdom .

OTHER PUBLICATIONS

Herbert O. House, Modern Synthetic Reactions, 2nd Ed. (1972), pp. 1-3.
Kuo et al, JACS, 93:23 (1971) pp. 6321-6323.
Dubois et al, Bull. Soc. Chim. Fr. (1963), pp. 1491-1496.
Ewing et al, J. Org. Chem., 40 (1975), pp. 2965-2966.
W. Carruthers, Some Modern Methods of Organic Synthesis, 2nd Ed., p. 2.
R. G. Pearson et al, JACS, 75 (1953), pp. 2439-2443.
Rathke et al, JACS, 93:9 (1971), pp. 2318-2320.
John C. Stowell, Carbanions in Organic Synthesis (1979), pp. 157-158.
Pfeffer et al, J. Org. Chem., vol. 37:3 (1972), pp. 451-458.
J. Herrmann et al, Tetrahedron Letters, No. 26 (1973), pp. 2429-2432.
Heathcock et al, J. Org. Chem., 45 (6) (1980), pp. 1066-1081.
Cregge et al, Tetrahedron Letters, No. 26 (1973), pp. 2425-2428.
M. Larcheveque et al, CA, 84:179576b.
Warner et al, J. Org. Chem. (1982), vol. 47, pp. 893-895.
G. Frater, Tetrahedron Letters (1981) 22(5), pp. 425-428.
D. Seebach et al, Helv. Chim. Acta, 63(1) (1980), pp. 197-200.
P. L. Creger, JACS, 89(10) (1967), pp. 2500-2501.

Primary Examiner—Norma S. Milestone
Attorney, Agent, or Firm—Joseph DiPrima; William H. Nicholson

[57] ABSTRACT

Mevinolin, compactin and dihydro- and tetrahydro derivatives thereof are converted to more active HMG-CoA reductase inhibitors by C-methylation of the natural 2(S)-methylbutyryloxy side chain to form a 2,2-dimethylbutyryloxy side chain.

6 Claims, No Drawings

PROCESS FOR C-METHYLATION OF 2-METHYLBUTYRATES

This is a continuation of application Ser. No. 540,954, filed Oct. 11, 1983, now abandoned.

SUMMARY OF THE INVENTION

This invention is concerned with a novel process which may be depicted as:

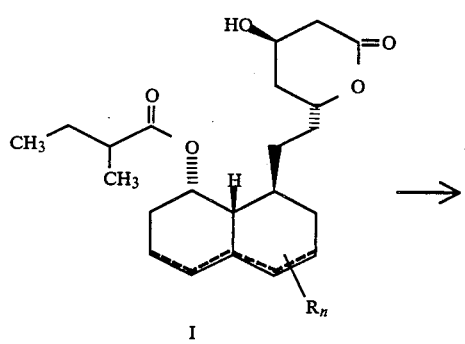

I

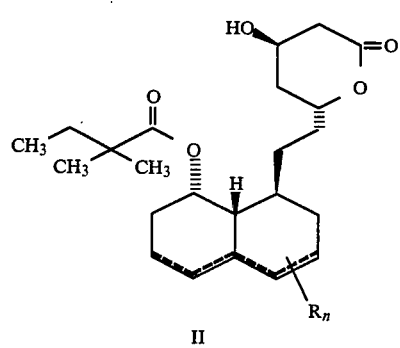

II

The products II, of the process are more active inhibitors of HMG-CoA reductase than are the starting Compounds I, and thus of greater utility in the treatment of atherosclerosis, hyperlipemia, familial hypercholesterolemia and like disorders.

BACKGROUND OF THE INVENTION

Compounds of structure I are known and known to have HMG-CoA reductase inhibitory properties. They are the natural fermentation products mevinolin (U.S. Pat. No. 4,231,938) and compactin (U.S. Pat. No. 3,983,140) and derivatives thereof, all with the natural 2-methylbutyrate side chain.

Hydrogenation products, including tetrahydromevinolin are described in U.S. Pat. No. 4,351,844.

Some compounds of structure II with the 2,2dimethylbutyrate side chain and processes for their preparation are known in EPO published application 33538. However, the process disclosed therein involves 4 distinct chemical steps: (1) de-esterification of the 2-methylbutyrate; (2) protection of the 4-hydroxy of the pyranone ring; (3) re-esterification to form the desired 2,2-dimethylbutyrate; and (4) deprotection of the 4-hydroxy group.

Now, with the present invention there is provided a novel process for the preparation of compounds of structure II involving only one chemical step and resulting in overall yields much higher than those realized by the prior art process, with the expenditure of much less time, labor and materials.

DETAILED DESCRIPTION OF THE INVENTION

The novel process of this invention may be represented by:

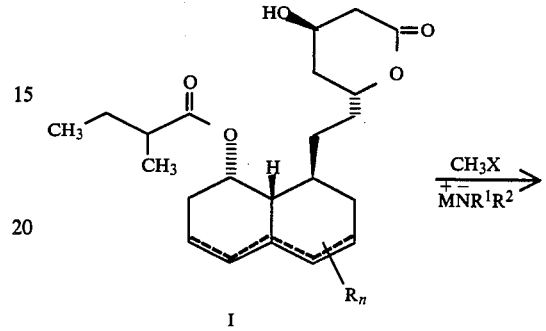

I

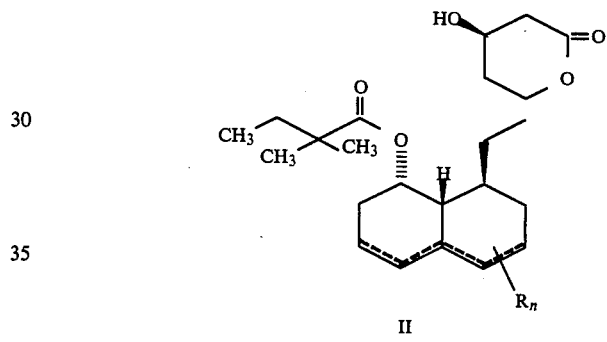

II wherein the dotted lines represent possible double bonds there being 0, 1 or 2 double bonds;

n represents 1, 2, 3 or 4; and

R is (1) methyl, (2) hydroxy, or (3) $C_{1-4}$ alkoxy, $R^1$ and $R^2$ are independently.

(1) $C_{1-3}$ alkyl, or (2) $R^1$ and $R^2$ joined together, form a 5 or 6-membered heterocycle such as pyrrolidine or piperidine with the nitrogen to which they are attached;

X is halo, such as chloro, bromo or iodo; and $M^+$ is a cation derived from lithium, sodium, or potassium.

A preferred use for the novel process of this invention is in the preparation of compounds of formula II wherein there is no double bond, one double bond in the 3,4-position, or two double bonds in the 3,4 and 4a,5 positions; n is 1 or 2; and R is methyl in the 2-position if n=1 and in the 2 and 6positions when n=2.

A most preferred use for the novel process is in the preparation of the compound of structural formula:

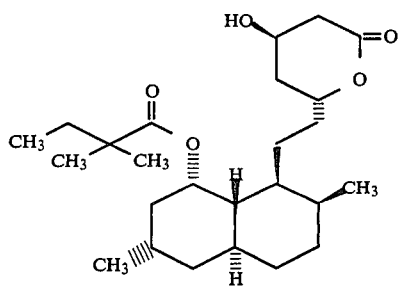

The novel process comprises C-methylation at the 2-position of the 2-methylbutyryloxy group of I at the 8-position of the polyhydronaphthalene moiety. The lactone compound is first converted to an alkali metal salt, preferably the potassium salt, of the dihydroxycarboxylate. Although any conceivable process for preparing a dry salt would suffice, it is convenient to add a substantially stoichiometric amount of aqueous potassium hydroxide to a solution of the lactone starting material in a hydrocarbon solvent such as benzene, toluene or cyclohexane containing a small amount of a C1-3 alkanol, preferably isopropanol, ethanol or methanol, stirring for a few minutes to about an hour and finally concentrating a dryness in vacuo. The residue is subjected to rigorous drying such as by azeotropic distillation with cyclohexane or toluene, as the actual methylation procedure that follows proceeds properly only under rigorously anhydrous conditions.

The dry alkali metal salt is dissolved in an ethereal solvent such as tetrahydrofuran, diethyl ether, 1,2-dimethoxyethane, or the like, cooled to about −50° to about −25° C., preferably −35° to −30° C., and treated with an excess of a strong base such as an alkali metal amide, wherein the alkali metal is lithium, sodium or potassium, preferably lithium, and the amide is diethylamide, pyrrolidide, dimethyl amide or diisopropyl amide in an ethereal solvent in a dry inert environment. After about 2 to 8 hours, preferably about 2 hours at about −50° to −25° C., preferably −35° to −30° C., a methylhalide, such as methylbromide, methylchloride or methyl iodide, preferably methyl bromide, or methyl iodide, is added to the mixture while maintaining the low temperature. Treatment with a strong base and methyl halide as described can be repeated if appreciable quantities of starting material remain. After about 0.5 to about 3 hours, following final addition of methyl halide the reaction mixture is quenched by adding it to an excess of water. To isolate the product the aqueous phase is adjusted to pH 3-6 with a strong mineral acid such as hydrochloric, hydrobromic, sulfuric, phosphoric acid or the like. The aqueous phase is extracted with cyclohexane or toluene, dried, filtered, refluxed for 3-20 hours and finally concentrated, and filtered.

EXAMPLE 1

Preparation of 6(R)-[2-[8(S) (2,2-dimethylbutyryloxy)-2(S),6(S)-dimethyl-1,2,3,4,4a(S), 5,6,7,8,8a(S)-decahydronaphthyl-1(S)]ethyl]-4(R)-hydroxy-3,4,5,6-tetrahydro-2H-pyran-2-one A solution of trans-tetrahydro mevinolin (5 g, 12.25 mmol) in cyclohexane (100 ml) and isopropanol (12 ml) was prepared under nitrogen. An aqueous solution of potassium hydroxide (4.91 M, 2.5 ml, 12.27 mmol) was added in one portion and the two-phase mixture stirred for 0.5 hr. at ambient temperature. The mixture was concentrated via distillation (bath temperature 100° C.). The vessel was recharged with 150 ml of cyclohexane and reconcentrated to a volume of 15 ml. The potassium carboxylate solution was diluted with tetrahydrofuran (35 ml) and cooled to −35° C.

A solution of pyrrolidine (3.6 ml, 43.1 mmol) in tetrahydrofuran (30 ml) was cooled to −5° C. and a solution of n-butyllithium (27.5 ml, 42.6 mmol, 1.55 M is hexane) was gradually added maintaining an internal temperature below 0° C. during the addition.

The lithium pyrrolidide thus prepared was added to the cooled solution of the potassium carboxylate via cannula, maintaining an internal temperature below −30° C. throughout the addition. The clear yellow solution was aged between −35° to −30° C. for 2 hours. A solution of methyl bromide (2.36, 24.8 mmol) in tetrahydrofuran was added maintaining an internal temperature of −20° C. The white slurry was aged for 1 hour at this temperature. A solution of pyrrolidine (1.6 ml, 19.16 mmol) in tetrahydrofuran (15 ml) was cooled to −5° C. and n-butyllithium (12 ml, 18.6 mmol, 1.55 M in hexane) was added maintaining the temperature below 0° C. This solution was gradually added to the reaction mixture maintaining an internal temperature below −30° C. The mixture was aged at −30° to −35° C. for 2 hours. A solution of methyl bromide (3.01 g, 31.7 mmol) in tetrahydrofuran was added maintaining an internal temperature of −20° C. The mixture was aged at that temperature for 1 hour.

The mixture was quenched into a vessel containing water (100 ml), the layers separated and the lower (aqueous) phase adjusted to pH 4.5 with 20% aqueous phosphoric acid. The acidified aqueous phase was extracted three times with 100 ml of cyclohexane. The combined cyclohexane extracts were washed twice with 50 ml of water, then dried over sodium sulfate (25 g). The mixture was filtered and slowly concentrated to a volume of 40 ml via distillation over 5 hours. After cooling to ambient temperature, the mixture was filtered to give crude product (4.15-4.25 g) of approximately 90-92% purity. The product was dissolved in methanol (22 ml/g of substrate) and water (6.2 ml/g) with stirring at 65° C. while additional water (6.2 ml/g) was added. The mixture was aged at ambient temperature overnight, filtered and dried under vacuum at 50° C. to yield pure product (85-92% recovery). Overall yield from trans-tetrahydro mevinolin is 67-75%.

EXAMPLE 2

Alternate Preparation of 6(R)-[2-[8(S) (2,2-dimethyl-butyryloxy)-2(S),6(S)-dimethyl-1,2,3,4,4a(S), 5,6,7,8,8a(S)-decahydronaphthyl-1(S)]ethyl]-4(R)-hydroxy-3,4-5,6-tetrahydro-2H-pyran-2-one A solution of trans-tetrahydro mevinolin (5 g, 12.25 mmol) in toluene (60 ml) and methanol (12 ml) was prepared in a 250 ml round bottom flask under nitrogen.

A titrated aqueous solution of potassium hydroxide (4.91M, 2.5 ml, 12.27 mmol) was added in one portion and the two-phase mixture stirred for 0.5 hour at ambient temperature.

The mixture was concentrated to dryness on a rotary evaportor (bath temperature 60°-75° C., 60-70 mm Hg). The vessel was recharged with 100 ml of toluene and reconcentrated. This recharge and concentration process was repeated providing a cream colored foam.

The dried potassium carboxylate was dissolved in tetrahydrofuran (45 ml) and cooled to −35° C.

A solution of diethylamine (4.5 ml, 43.5 mmol) in tetrahydrofuran (30 ml) was cooled to −25° C. and a solution of n-butyllithium (27.5 ml, 42.6 mmol, 1.55 M in hexane) was gradually added maintaining an internal temperature below −20° during the addition.

The lithium diethylamide thus prepared was added to the cooled solution of the potassium carboxylate via cannula, maintaining an internal temperature below −30° C. throughout the addition. The clear yellow solution was aged between −35° to 30° C. for 5 hours.

Methyl iodide (1.4 ml, 22.5 mmol) was added dropwise maintaining an internal temperature of −30° C. The white slurry was aged for 1 hour at this temperature.

A solution of diethylamine (2 ml, 19.3 mmol) in tetrahydrofuran (15 ml) was cooled to −25° C. and n-butyllithium (12 ml, 18.6 mmol, 1.55 M in hexane) was added, maintaining the temperature below −20° C. This solution was gradually added to the reaction mixture maintaining an internal temperature below −30° C. The mixture was aged at −30° to −35° C. for 2 hours.

Methyl iodide (2 ml, 32.13 mmol) was added maintaining an internal temperature of −30° C. The mixture was aged at that temperature for 1 hour.

The mixture was quenched into a vessel containing toluene (200 ml) and water (100 ml).

The mixture was adjusted to pH 4.5 with 20% aqueous phosphoric acid (approx. 30 ml). The layers were separated and the upper (organic) phase stirred over sodium sulfate (25 g) and sodium bisulfite (1.5 g) for 2 hours. The mixture was filtered through Supercel$^R$ and transferred to a 500 ml round bottom flask, fitted with a distillation head and heated for 6-10 hours (bath temperature 110° C.).

The toluene solution was concentrated to dryness to give crude product (5.3-5.4 g). Crude product was stirred in refluxing cyclohexane (50 ml) for 1 hour then allowed to cool with stirring to room temperature and aged an additional 1 hour, filtered and dried under vacuum at 50° C. to yield product (3.4-3.8 g) of approximately 90-92% purity.

The product was dissolved in methanol (22.6 ml/g of substrate) and water (6.2 ml/g) with stirring at 65° C. The solution was filtered then heated at 65° C. while additional water (6.2 ml/g) was added. The mixture was aged at ambient temperature overnight, filtered and dried under vacuum at 50° C. with a nitrogen purge to yield pure product (85-92% recovery). Overall yield from trans-tetrahydro mevinolin is 58-62%.

EXAMPLE 3

Alternate Preparation of 6(R)-[2-[8(S) (2,2-dimethyl-butyryloxy)-2-(S),6(S)-dimethyl-1,2,3,4,4a(S), 5,6,7,8,8a(S)-decahydronaphthyl-1(S)]ethyl]-4(R)-hydroxy-3,4,5,6-tetrahydro-2H-pyran-2-one The potassium salt of trans-tetrahydromevinolin (20 g, 49 mmole) is prepared in cyclohexane (400 ml), isopropanol (48 ml) and aqueous potassium hydroxide (10 ml, 4.91 molar) as described above. The mixture is concentrated by distillation at atmospheric pressure. Additional cyclohexane (450 ml) is added. A total of 600 ml of distillate is collected. A KF of less than 70 μg H₂O/ml should be observed. The mixture is concentrated to a total volume of 52 ml.

Tetrahydrofuran (280 ml) and pyrrolidine (16 ml) is charged into the vessel and the solution cooled to less than −55° C. Butyllithium (110 ml, 1.55 M) is slowly added to the well stirred mixture, maintaining an internal temperature below −55° C. throughout the addition. The mixture is aged at −30° to −35° C. for 2.5 hours. Methylbromide (10.0 g) is bubbled into the solution maintaining an internal temperature of −20° to −25° C. After an age of 15 minutes HPLC analysis is performed to confirm greater than 93% conversion. If less than 93% conversion is observed a second charge of methyl bromide (normally 0.25-0.75 g) is introduced. The mixture is aged at −20° to −25° C. for a total of one hour.

Tetrahydrofuran (60 ml) and pyrrolidine (6.4 ml) are charged to the reaction mixture and cooled to less than −55° C. n-BuLi (48 ml, 1.55 M) is slowly added as before maintaining an internal temperature below −55° C. during the addition. The mixture is aged for two hours at −30° to −35° C. Methyl bromide (12 g) is introduced as described above and the mixture aged for 1 hour at −20° to −25° C. The reaction mixture is quenched into 400 ml of H₂O and worked up and relactonized as described above. The crude yield after filtration of cyclohexane slurry and drying (40° C. in vacuo) 17.89 g, 86.9% pure. Overall yield is 75.2%.

Employing the procedure substantially as described in Examples 1 and 2, but substituting for the trans-tetrahydromevinolin used as starting material therein, approximately equimolecular amounts of the 2-methylbutyrates described in Table I, there are prepared the 2,2-dimethylbutyrate products, also described in Table I:

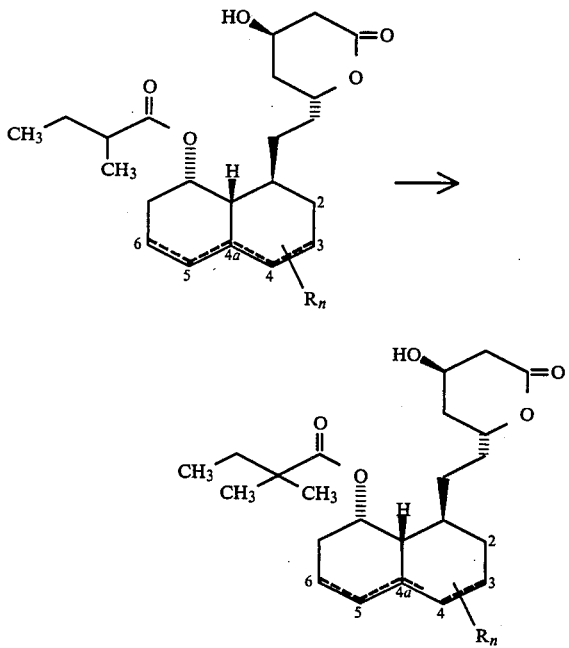

TABLE I

| DOUBLE BONDS | Rn |
| --- | --- |
| 3,4:4a,5 | 2-CH₃, 6-CH₃ |
| 3,4 | 2-CH₃, 6-CH₃ |
| 4,4a | 2-CH₃, 6-CH₃ |

TABLE I-continued

| DOUBLE BONDS | Rn |
| --- | --- |
| 4a,5 | 2-CH$_3$, 6-CH$_3$ |
| 3,4:4a,5 | 2-CH$_3$ |
| 3,4 | 2-CH$_3$ |
| — | 2-CH$_3$ |
| 3,4:4a,5 | 2-CH$_3$, 6-OH |
| 4,4a | 2-CH$_3$, 3-OH, 5-OH |
| 4,4a:5,6 | 2-CH$_3$, 3-OH |
| 4,4a | 2-CH$_3$ |
| 4a,5 | 2-CH$_3$ |
| — | 2-CH$_3$, 6-OH |
| — | 2-CH$_3$, 3-OH |
| 4,4a | 2-CH$_3$, 6-OH |
| 4,4a | 2-CH$_3$, 3-OH |
| 4a,5 | 2-CH$_3$, 6-OH |
| 4a,5 | 2-CH$_3$, 3-OH |
| 4,4a:5,6 | 2-CH$_3$, 3-OCH$_3$ |
| — | 2-CH$_3$, 3-OH, 5-OH |
| 4.4a | 2-CH$_3$, 3-Cl, 5-Cl |
| 4.4a | 2-CH$_3$, 3-OC$_2$H$_5$, 5-OH |
| 4.4a | 2-CH$_3$, 3-OC$_4$H$_9$, 5-OH |
| 4.4a | 2-CH$_3$, 6-CH$_3$, 3-OH, 5-OH |

What is claimed is:

1. A process for the preparation of a compound of the structural formula IIA:

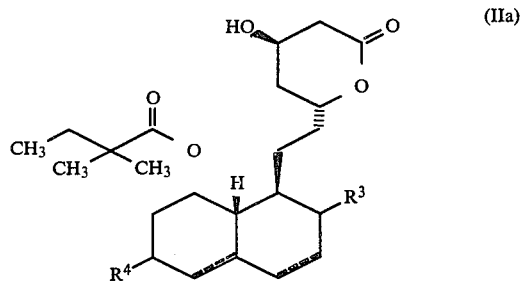

wherein:
R$^3$ is methyl;
R$^4$ is hydrogen, methyl or hydroxy; and the dotted lines represent possible double bonds in the 3,4-position, in the 3, 4 and 4a, 5 position or there are no double bonds.

which comprises treatment of a compound of the structural formula (Ia):

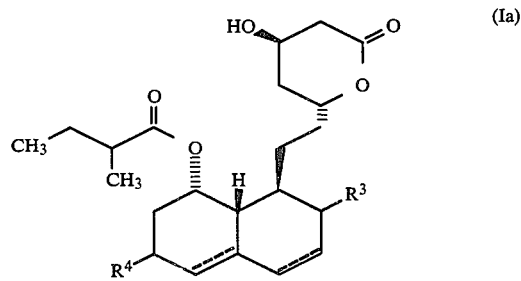

as its alkali metal salt with a methyl halide and an alkali metal amide of the formula $$M^+N^-R^1R^2$$

wherein M$^+$ is a cation derived from sodium, potassium or lithium, and
R$^1$ and R$^2$ are C$_{1-3}$alkyl or when taken together with the nitrogen atom to which they are attached form a 5 or 6 membered heterocyclic ring;
followed by acidification and lactonization.

2. The process of claim 1 which comprises treatment of Compound Ia with methyl iodide or methyl bromide in an ethereal solvent at $-60°$ to $-25°$ C.

3. The process of claim 2 wherein the ethereal solvent is tetrahydrofuran, the temperature is $-35°$ to $-30°$ C. and the alkali metal amide is lithium diethylamide or lithium pyrrolidide.

4. The process of claim 1 for the preparation of the compound of formula:

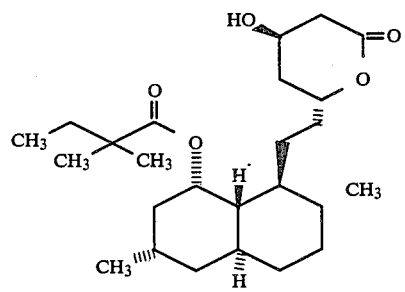

5. The process of claim 2 for the preparation of the compound of formula:

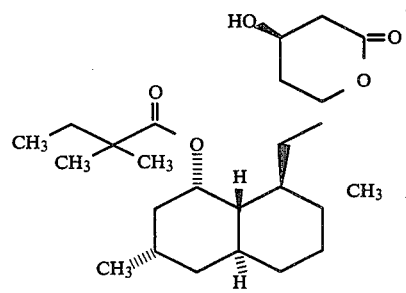

6. The process of claim 3 for the preparation of the compound of formula:

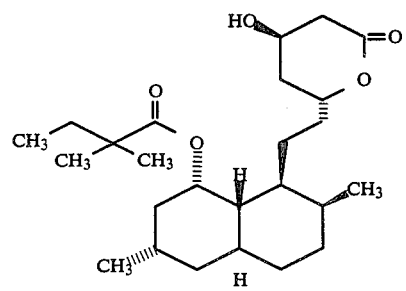

* * * * *

UNITED STATES PATENT AND TRADEMARK OFFICE
CERTIFICATE OF CORRECTION

PATENT NO. : 4,582,915

DATED : April 15, 1986

INVENTOR(S) : M. Sletzinger, T. R. Verhoeven, R. P. Volante

It is certified that error appears in the above—identified patent and that said Letters Patent is hereby corrected as shown below:

Title page, Item [19] and [75]:

One of Applicants' names is misspelled. Correct spelling is: Meyer Sletzinger

Signed and Sealed this

Twenty-ninth Day of December, 1987

Attest:

DONALD J. QUIGG

Attesting Officer     Commissioner of Patents and Trademarks